(12) United States Patent
Olson et al.

(10) Patent No.: US 8,252,711 B1
(45) Date of Patent: *Aug. 28, 2012

(54) SELF SUPPORTING STRUCTURALLY ENGINEERED NON-PLATINUM ELECTROCATALYST FOR OXYGEN REDUCTION IN FUEL CELLS

(75) Inventors: Tim Olson, Albuquerque, NM (US); Plamen Atanassov, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 231 days.

This patent is subject to a terminal disclaimer.

(21) Appl. No.: 12/709,618

(22) Filed: Feb. 22, 2010

Related U.S. Application Data

(63) Continuation of application No. 11/872,836, filed on Oct. 16, 2007, now Pat. No. 7,678,728.

(60) Provisional application No. 60/852,060, filed on Oct. 16, 2006.

(51) Int. Cl.
B01J 31/00 (2006.01)
C07D 487/22 (2006.01)
C07B 47/00 (2006.01)
B05D 5/12 (2006.01)

(52) U.S. Cl. .................. 502/164; 540/145; 427/115

(58) Field of Classification Search .................. None
See application file for complete search history.

(56) References Cited

U.S. PATENT DOCUMENTS 7,678,728 B2 * 3/2010 Olson et al. ............ 502/164

* cited by examiner

Primary Examiner — Emily Le
Assistant Examiner — Michael Forrest
(74) Attorney, Agent, or Firm — Gonzales Patent Services; Ellen M. Gonzales

(57) ABSTRACT

A highly dispersed, unsupported, electrocatalyst made of pyrolyzed porphyries and a method for synthesizing the same. The disclosed synthesis procedure allows for optimization of pore size and therefore transport properties. Compounds suitable for use include transition metal $N_4$-chelates such as, but not necessarily limited to, $N_4$-chelates containing different metal centers including Co, Fe, Mn, Ni, Ru, Cu, etc., and other $N_4$-chelates such as porphyrin, phthalocyanies, and structures based on their pyro products.

12 Claims, 13 Drawing Sheets

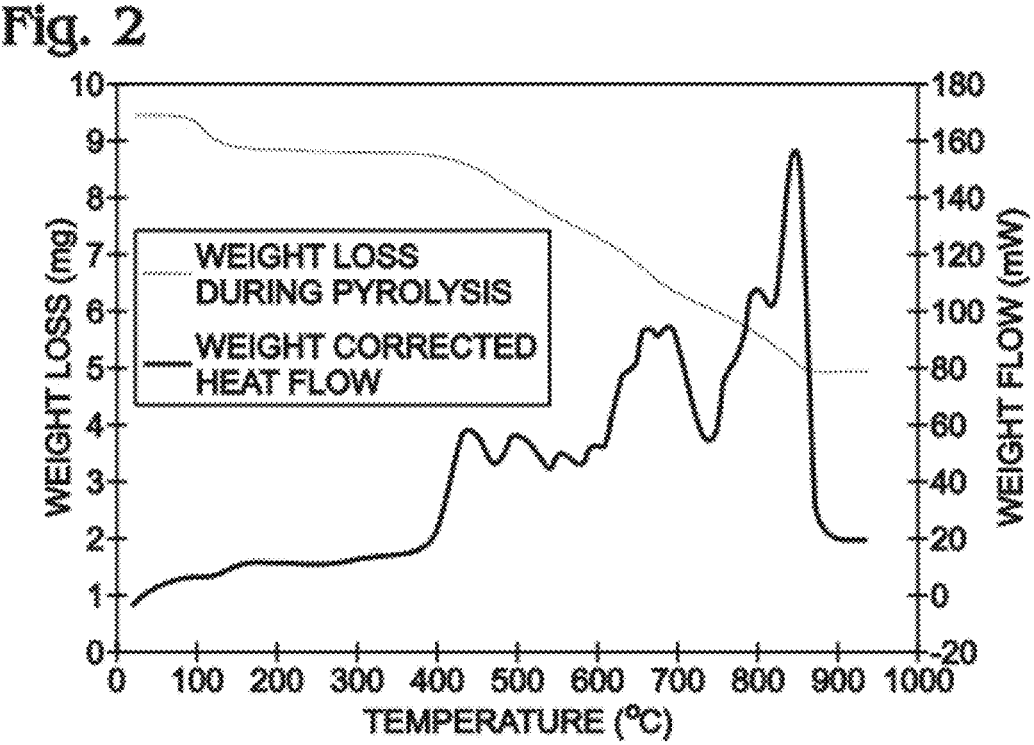
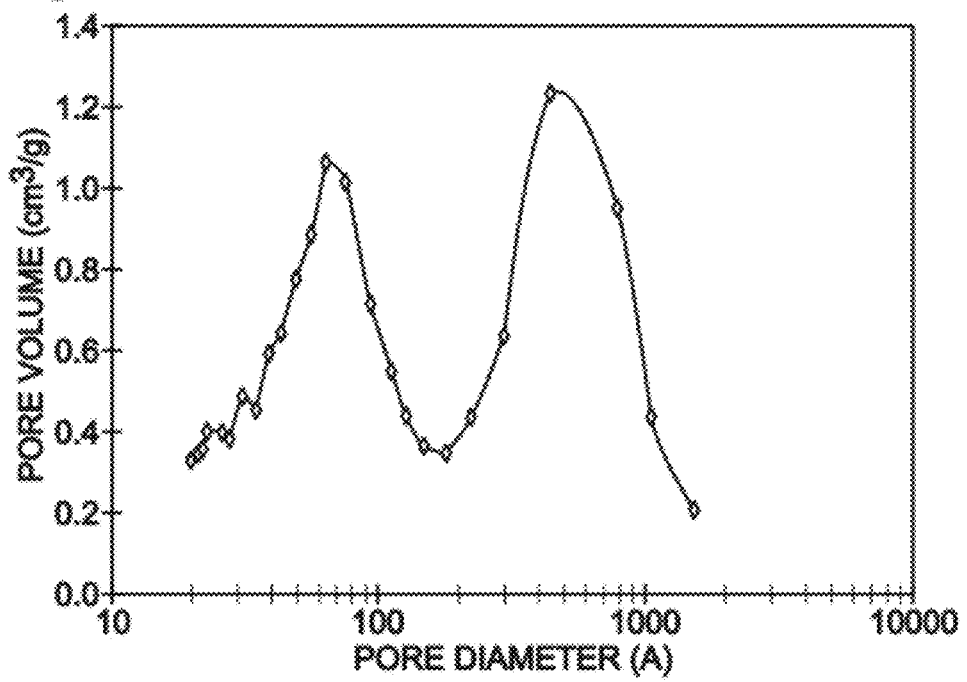

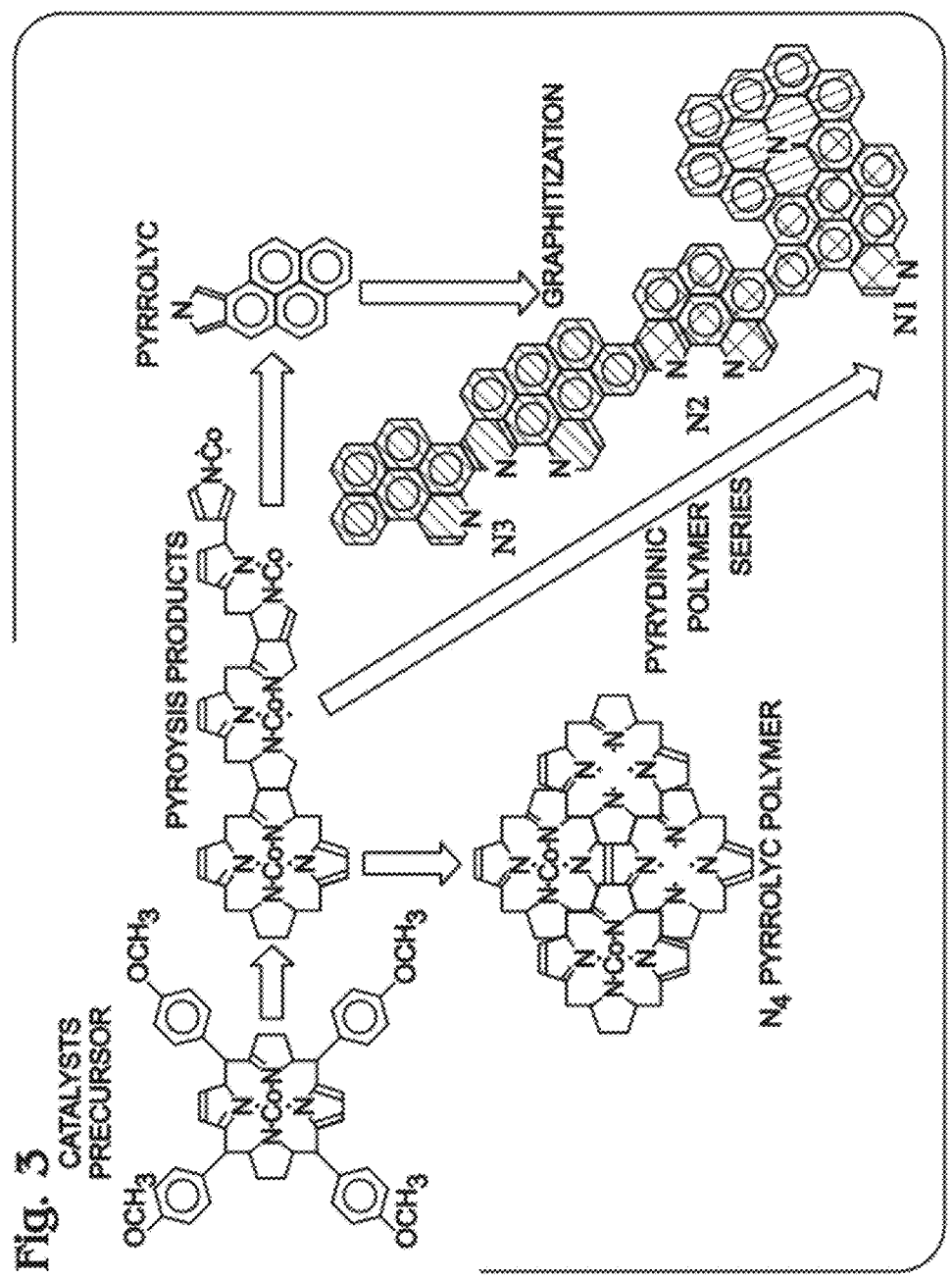

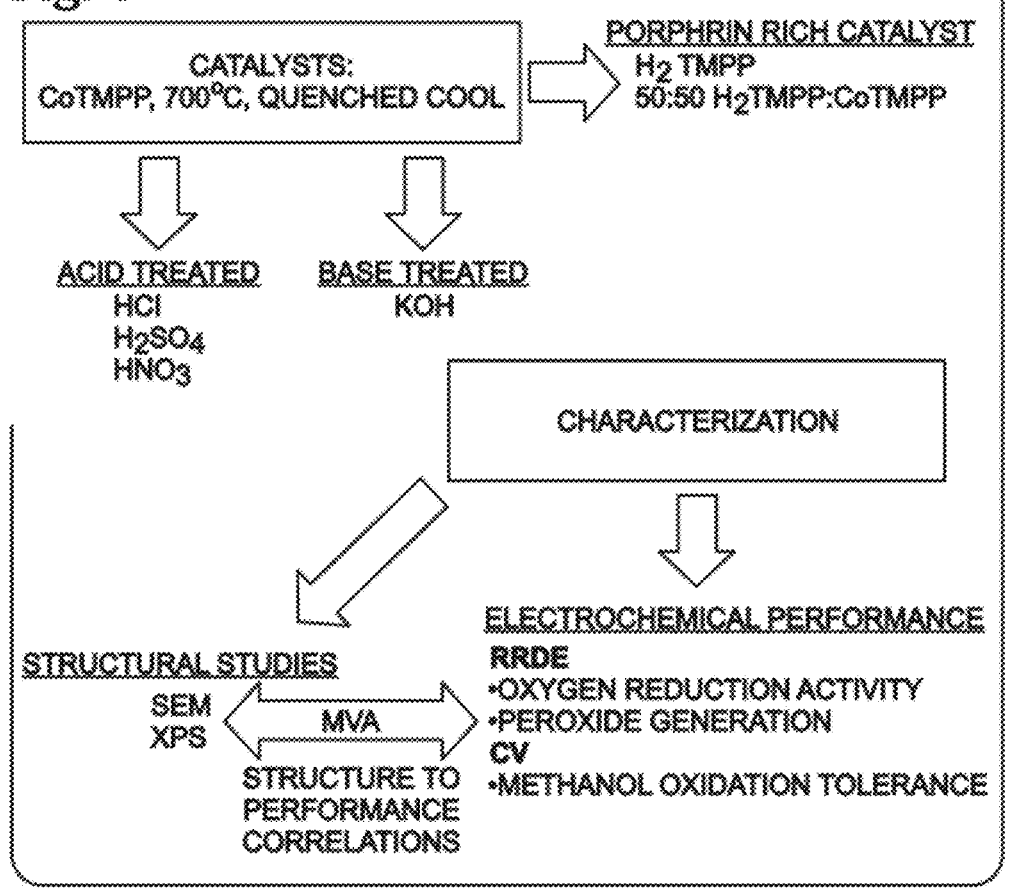
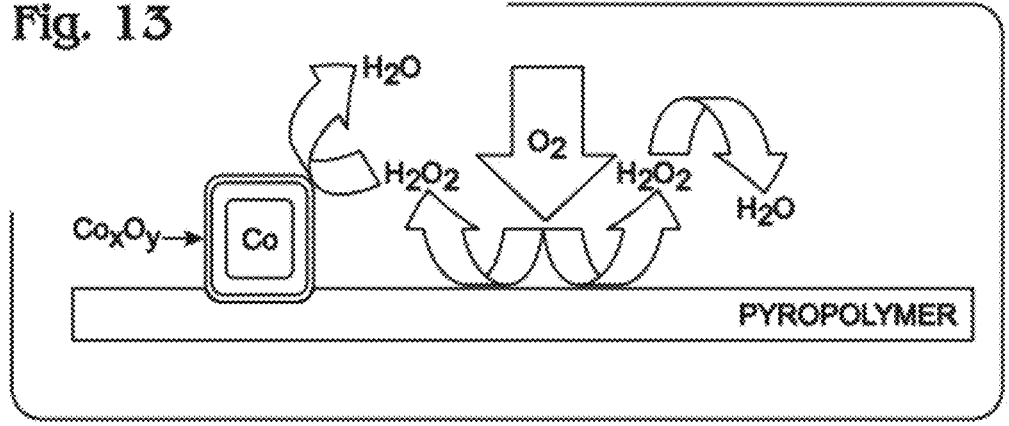

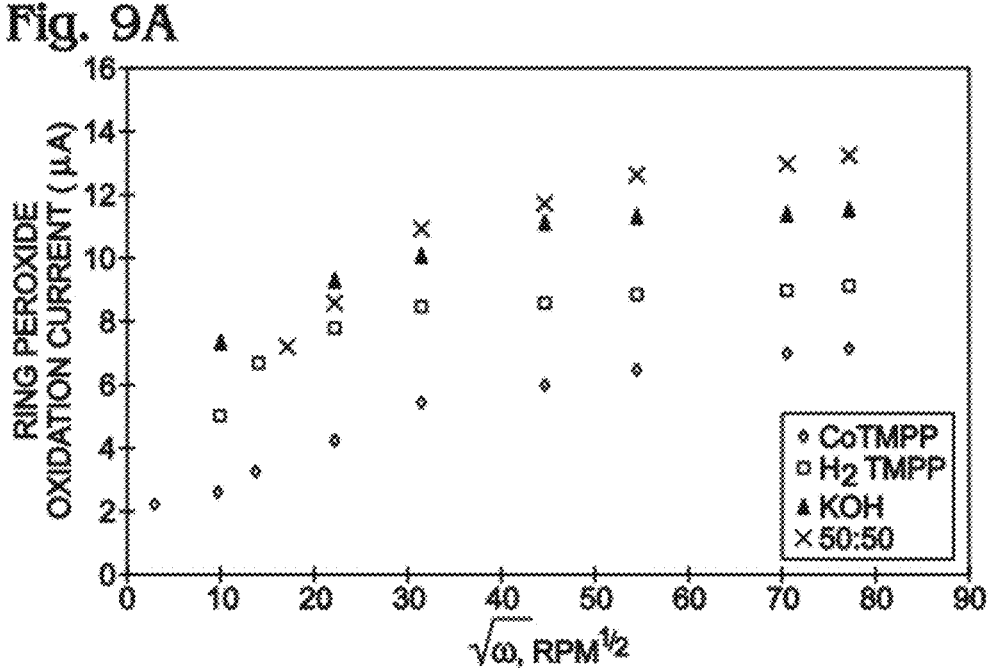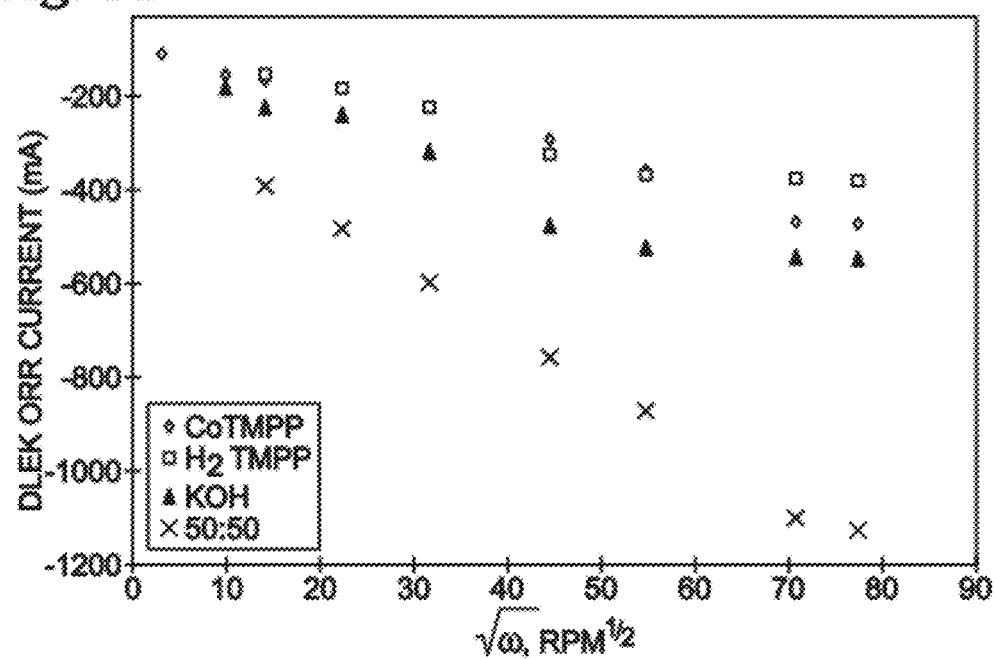

Fig. 11A CoTMPP
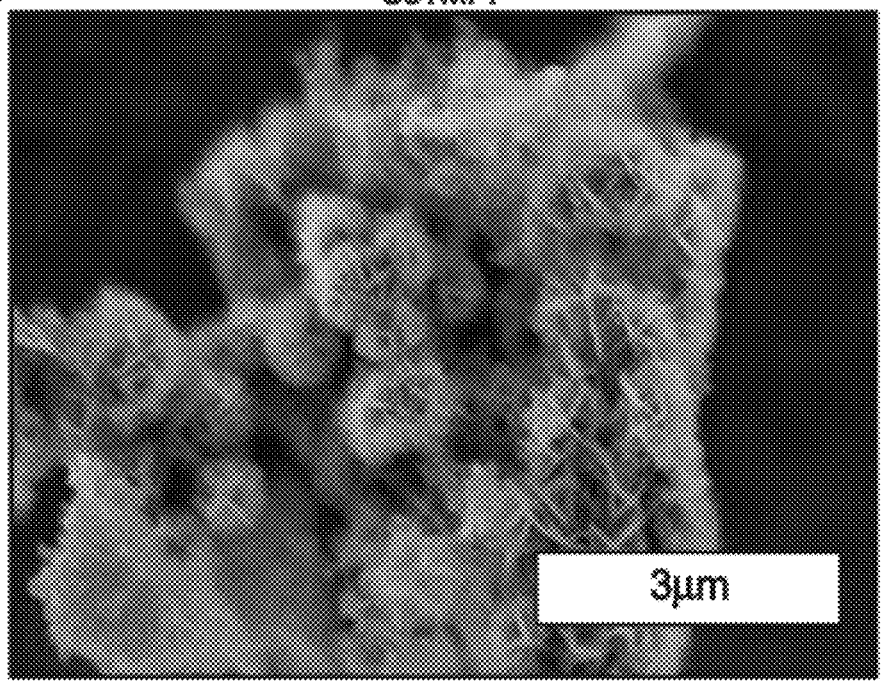
Fig. 11B 50:50 H₂TMPP:CoTMPP
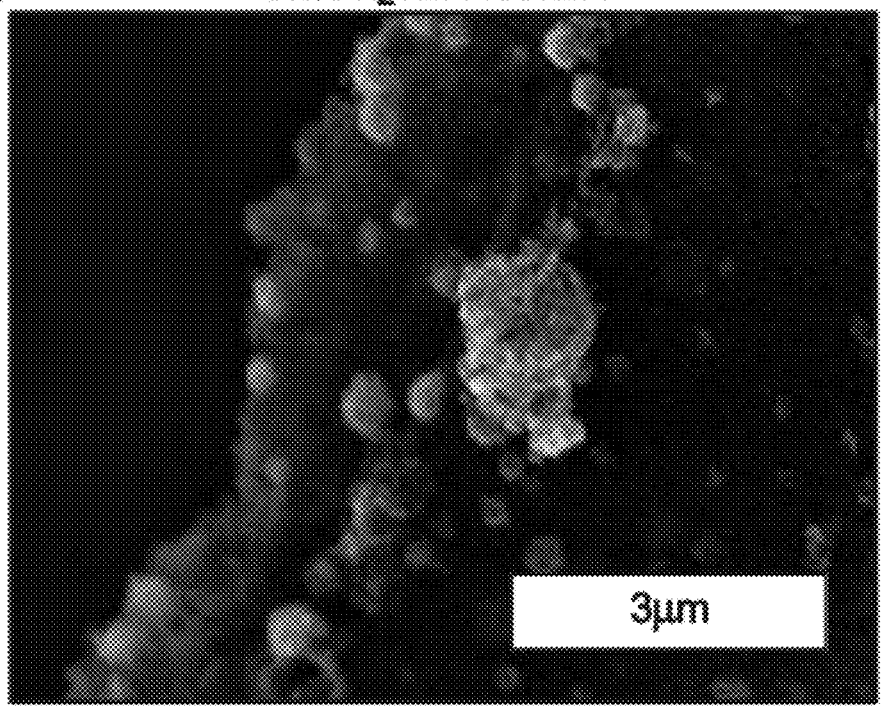

SELF SUPPORTING STRUCTURALLY ENGINEERED NON-PLATINUM ELECTROCATALYST FOR OXYGEN REDUCTION IN FUEL CELLS

CROSS-REFERENCE TO RELATED APPLICATIONS

The following application is a continuation of U.S. patent application Ser. No. 11/872,836 filed Oct. 16, 2007 which claims benefit of U.S. Provisional Application No. 60/852,060, filed Oct. 16, 2006, both of which are hereby incorporated by reference in the entirety.

STATEMENT REGARDING GOVERNMENT SPONSORED RESEARCH

This invention was made with government support under Grant No. 74004S, awarded by the Army Research Office. The government has certain rights in the invention.

BACKGROUND

Fuel cells are receiving increasing attention as a viable energy-alternative. In general, fuel cells convert electrochemical energy into electrical energy in an environmentally clean and efficient manner. Fuel cells are contemplated as potential energy sources for everything from small electronics to cars and homes. In order to meet different energy requirements, there are a number of different types of fuel cells in existence today, each with varying chemistries, requirements, and uses.

As one example, Direct Methanol Fuel Cells (DMFCs) rely upon the oxidation of methanol on an electrocatalyst layer to form carbon dioxide. Water is consumed at the anode and produced at the cathode. Positive ions (H+) are transported across a proton exchange membrane to the cathode where they react with oxygen to produce water. Electrons can then be transported via an external circuit from anode to cathode providing power to external sources.

As another example, polymer electrolyte membrane (PEM) fuel cells (also called proton exchange membrane fuel cells) use pure hydrogen (typically supplied by a hydrogen tank) as a fuel. A stream of hydrogen is delivered to the anode side of a membrane-electrode assembly (MEA), where it is catalytically split into protons and electrons. As with the DMFC, the positive ions are transported across a proton exchange membrane to the cathode where they react with oxygen to produce water.

Currently, one of the limiting factors in the wide scale commercialization of PEM and DMFC fuel cells is the cost associated with precious metals. Both DMFC and PEM fuel cells commonly use platinum as an electrocatalyst. Nobel metals such as platinum are needed to catalyze the sluggish oxygen reduction reaction (ORR) at the cathode. One of the major routes to overcome this limitation is to increase the platinum utilization in noble-metal based electrocatalysts. Another viable route is to use a less expensive, yet still sufficiently active catalyst in larger quantities. Several classes of non-platinum electrocatalysts have been identified as having adequate oxygen reduction activity to be considered as potential electrocatalysts in commercial fuel cell applications.

Generally, known non-platinum electrocatalysts are supported on high surface area carbon blacks. This is done to increase dispersion, active surface area, and conductivity of the catalytic layer. The synthesis procedure usually includes precipitation of the precursor molecules onto the supporting substrate and pyrolyzation of the supported precursor.

BRIEF DESCRIPTION OF THE DRAWINGS

FIG. 2 depicts TGA analysis of pyrolyzation of CoTMPP prepared according to methods described in the present disclosure.

FIG. 3 depicts possible moieties that may be incorporated in a pyropolymer backbone.

FIG. 6 is a BJH adsorption dV/dlog(D) pore volume plot for CoTMPP templated on Cabosil silica according to an exemplary method of the present disclosure.

FIG. 7 is a schematic flowchart of an exemplary method according to the present disclosure for determining the ORR mechanism for non-platinum electrocatalysts.

FIG. 9a is a Koutecky-Levich plots for RRDE experiments according to the present disclosure showing peroxide oxidation at the ring electrode.

FIG. 9b is a Koutecky-Levich plots for RRDE experiments according to the present disclosure showing oxygen reduction at the disk electrode as a function of the square root of rotation speed.

FIG. 11a shows SEM images of CoTMPP.

FIG. 11b shows SEM images of 50:50 wt % CoTMPP:$H_2$TMPP.

FIG. 13 illustrates a proposed ORR mechanism for electrocatalysts of the current disclosure.

DETAILED DESCRIPTION

According to a first embodiment, the present disclosure provides a method for manufacturing a self-supporting non-platinum electrocatalyst. In general, a catalytic precursor is first templated on a supporting structure, pyrolyzed, and then the support material is removed. The result is a self-supporting open-pore structure of only catalytic material.

According to another embodiment, the present disclosure also provides a non-platinum electrocatalyst formed by the methods described above. As stated above, the methods described herein result in a highly disperse non-supported metallic electrocatalyst wherein porosity is engineered in a repeatable and predictable fashion. Furthermore, using the method described herein the pore size, and therefore transport properties, of the electrocatalyst can be optimized.

Figure 1:
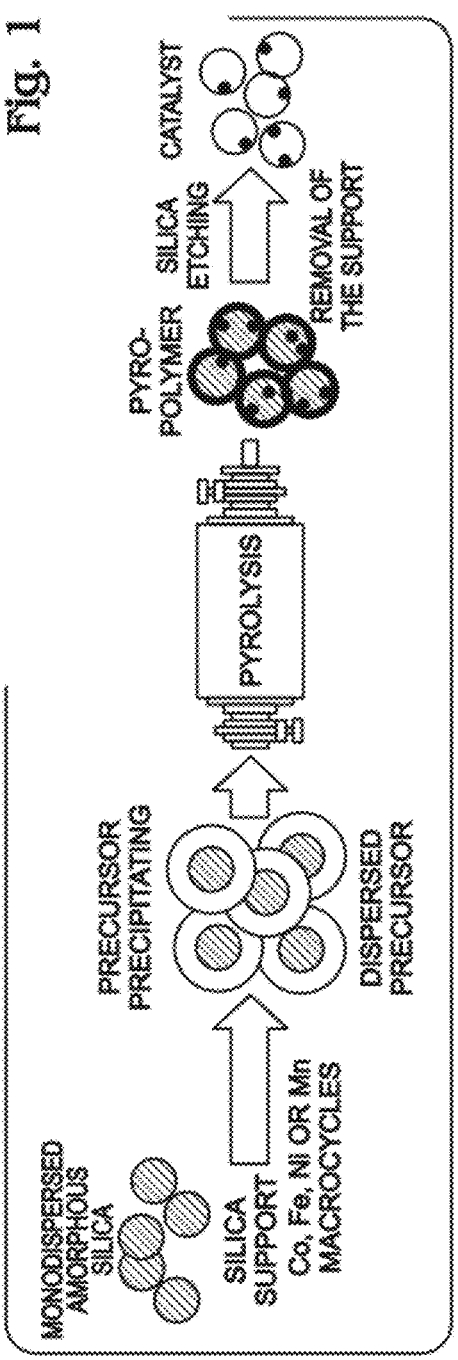
FIG. 1 depicts an exemplary embodiment of a method for producing a self-supporting non-platinum electrocatalyst according to the present disclosure.

An exemplary embodiment of a method according to the present disclosure is shown in FIG. 1. As shown in FIG. 1 precursor molecules are precipitated onto a removable support. Suitable precursor molecules may be selected from the group of transition metal $N_4$-chelates including, for example, but not limited to cobalt tetraphenyl porphyrin (CoTPP), cobalt tetramethoxyphenly porphyrin (CoTMPP), and other $N_4$-chelates containing different metal centers including such as Cobalt (Co), Iron (Fe), Nickel (Ni), Manganese (Mn), Ruthenium (Ru), Copper (Cu), etc, and other $N_4$-chelates such as porphyrins, phthalocyanies, and structures based on their pyro products. The removable support may take the form, for example, of monodispersed, amorphous, silica particles (fumed, meso-porous, etc.) or other removable templates. The dispersed precursor is then subjected to a controlled temperature conversion in an inert gas atmosphere (pyrolysis) to produce a pyropolymer. Exemplary inert gases suitable for use in the presently-disclosed embodiment include, but are not necessarily limited to nitrogen, argon and helium. The silica support is then removed, for example via exposure to a strong acid or base, to produce a self-supporting open-pore structure made only of catalytic material.

As stated above, the precursor molecules are precipitated onto silica particles and, as shown, the silica particles form the template on which the electrocatalyst is formed. While in some embodiments it may be desirable for the silica particles to be monodisperse, in other embodiments it may be desirable to use silica particles of varying sizes or even shapes (spheres, ovoids, irregular shapes, etc). It should be appreciated that the size and shape of the silica particles may be selected according to the desired shape(s) and size(s) of the voids within the electrocatalyst material. Accordingly, by selecting the particular size and shape of silica particles, one can produce a electrocatalyst having voids of a predictable size and shape. For example, if the silica particles are spheres, the electrocatalyst will contain a plurality of spherical voids. Those of skill in the art will be familiar with the electrocatalyst Pt—Ru black, which consists of a plurality of platinum-ruthenium alloy spheres. An electrocatalyst formed from using silica spheres with the above-described method looks like a negative image of the Pt—Ru black; the space that existed as a void in the Pt—Ru black is filled with metal electrocatalyst, and the space that existed as metal electrocatalyst in the Pt—Ru black is void.

As stated above, according to some embodiments, silica spheres of any diameter may be used. In some preferred embodiments, silica particles having an characteristic lengths of between 1 nm and 100 nm, in more preferred embodiments, silica particles having an characteristic lengths of between 100 nm and 1000 nm may be used and in other preferred embodiments, silica particles having an characteristic lengths of between 1 μm and 10 μm may be used. Further mesoporous silica can also be used in the templating synthesis approach. In this case the templating involves intercalating the mesopores of the material and results in a self-supported electrocatalysts with porosity in the 2-20 nm range. In one particular embodiment, the silica template is Cabosil amorphous fumed silica (325 $m^2/g$). As stated above, because the spheres serve as the template for the formation of the electrocatalyst, in an embodiment where silica particles having an average diameter of 20 nm is used, the spherical voids in the electrocatalyst will typically have a diameter of approximately 20 nm. Those of skill in the art will be familiar with a variety of silica particles that are commercially available, and such particles may be used. Alternatively, known methods of forming silica particles may be employed in order to obtain particles of the desired shape and/or size.

An X-ray photoelectron spectroscopy (XPS) study of the pyrolyzed material revealed that approximately half of the metal centers (cobalt tetra-phenyl porphyrin) remain associated to 1, 2, 3, or 4 nitrogen atoms in the 2+ form. The balance metal is found in a cobalt particle phase with a thin oxide layer on its surface. The pryopolymer which consists of carbon, nitrogen, and cobalt associated with nitrogen can be viewed as the backbone of the electrocatalyst material.

Thermal gravimetric analysis (TGA) was preformed under the same pyrolyzation synthesis conditions (i.e. nitrogen atmosphere, 3 C/min ramp rate, 700 C pyrolyzation temperature) for cobalt tetramethoxy-phenyl porphyrin (CoTMPP). FIG. 2 indicates that at least four distinct processes occur during pyrolyzation. An initial weight loss is detected at approximately 100° C., corresponding to moisture loss. Then a steady weight loss is observed between 400° C. and 850° C. Heat flow analysis suggests that at least three separate processes occur. Without additional MS analysis it can only be speculated that the first two increases in heat flow correspond to the decomposition of the O—$CH_3$ and phenyl groups, respectively. The third increase in heat flow could represent further decomposition of the precursor.

Figure 5:
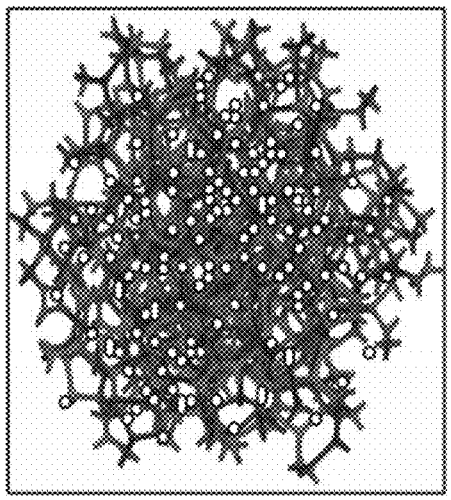
FIG. 5 is an illustration of a catalyst structure formed according to an exemplary method of the present disclosure
Figure 4:
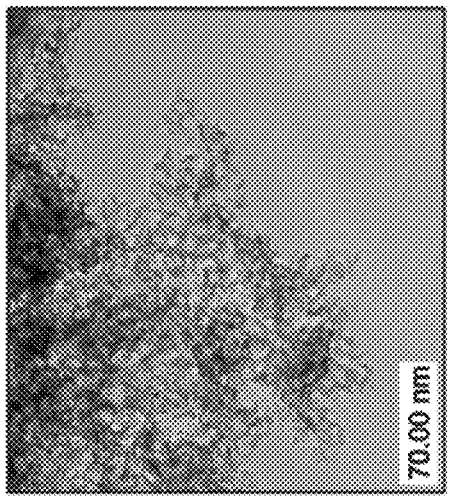
FIG. 4 is a TEM image of an electrocatalyst structure formed according to an exemplary method described in the present disclosure.

During pyrolyzation, depending on the degree of decomposition of the precursor molecule a number of different moieties can be formed. FIG. 3 shows the different moieties that can be formed, beginning with intact N4 centers resulting from low degree of decomposition. Further decomposition leads to the pyridinic nitrogen series and addition decomposition results in the formation of pyrrolic nitrogen species. Finally, FIG. 4 shows a TEM image of the pyrolyzed non-platinum electrocatalyst material after removal of template. FIG. 5 is a cartoon depiction of the electrocatalyst. The open porous network of pyropolymer is clearly shown. The cobalt particles with a thin oxide layer are shown as open circles.

The particle size distribution is an important factor when considering processes that occur in the active layer. The porosity, tortuosity, and active surface area are all dependent on the particle size distribution. Equation 1 illustrates the dependence of porosity $\xi$ and tortuosity $\tau$ on effective diffusivity $D_{eA}$.

$$D_{eA} = \frac{\xi}{\tau} D_A \quad \text{[Equation 1]}$$

To maximize the effective diffusivity in the active layer the porosity to tortuosity ratio also must be maximized. Ultrasonic atomizers have been reported to generate particles with diameters from 1 to 10 μm (mass mean diameter) and generally can be modeled with a standard distribution. The porosity to tortuosity ratio as well as active surface area both can be adjusted by using particles of different diameters.

A cascade impactor can be used to separate the batches of particles into discrete bunches of different particle sizes. The cascade impactor is able to separate particles based on aerodynamic size. This is achieved by passing an aerosol through a nozzle with the outlet directed at a flat plate. Smaller particles follow the stream line around the flat plate but larger particles that have inertia larger than a critical value will leave the steam line and can be collected on the flat plate. Putting a number of flat plates in series and varying the distance between the nozzle outlets and the flat plates allows separation of particle into bunches of discrete sizes. The performance of particles with monodispersed, standard, and bimodal distributions can be evaluated and optimized under MEA conditions.

The active site density can be further increased by engineering a porous electrocatalyst. This can be achieved by using the templating method that is described above. The active surface area is increased in two ways. First, the surface area of the porous structure can greatly increase the overall surface area. Second, the porous structure could increase transport properties allowing for a thicker active layer and therefore higher active site density (sites/cm3). The pore size distribution as well as the overall structure of the electrocatalyst can be manipulated by using silica templates with different characteristic sizes. For example, templating CoTMPP on Cabosil amorphous fumed silica (325 m²/g) in the batch synthesis procedure resulted in a pore size distribution as shown in FIG. 6, which shows a BJH adsorption dV/dlog(D) pore volume plot. As a result of the synthesis procedure a bimodal distribution is observed. It is believed that the pores in the size range of 3 to 10 nm results from processes that occur during pyrolyzation. While the pores in the size range of 30 to 70 nm results from characteristic dimensions of the silica template after its removal.

Electrocatalyst properties such as active surface area, characteristic diffusion lengths, and diffusion coefficients are all dependent on the overall electrocatalyst structure. Diffusion coefficients in the Knudsen region are a function of pore radius as given in Equation 2.

$$D_{KA} = \frac{4}{3} r \left( \frac{2}{\pi} \frac{RT}{MW_A} \right)^{\frac{1}{2}} \quad \text{[Equation 2]}$$

Because transport mechanisms and active surface area depend on pore size distribution, diffusion and reaction rates are also affected. The local variation in diffusion rates due to pore size distributions makes it very difficult to accurately predict the performance of porous electrocatalysts. Table A is a non-comprehensive list of possible silica templates. It shows that there is a wide variety of silica products with a range of particle diameters, surface areas, and pore size distributions.

Further, mesoporous silica can be fabricated with different types of pore architecture, including 1-D straight, 1-D tortuous, and 3-D interconnected pores. These materials provide templates that can vary the porosity to tortuosity ratio, diffusion coefficients, and therefore accessible active surface area. Table A compares the template and electrocatalyst specs for the Cabosil and mesoporous silica powders. Electrocatalyst specs are based on experimental data for the Cabosil template and a range of anticipated values is given for the mesoporous silica. Further, diffusion coefficients for the pore sizes and Thiele Modulus values are given for different rates of reaction. Two Thiele Modulus values are given for each specific reaction rate constant. The two values represent the high and low Thiele Modulus values for the given conditions. For example, the largest pore length and smallest diffusion coefficient and the shortest pore length and largest diffusion coefficient were used to calculate the two Thiele Modulus values.

It will be appreciated that it is important to maintain both macro porosity and Knudsen diffusion in the active layer. Macro diffusion between particles will allow for thicker active layer. While, porous structures within the electrocatalysts themselves increase the active surface area.

According to yet another embodiment, an experimental procedure is provided herein to elucidate the oxygen reduction reaction (ORR) mechanism that occurs on non-platinum electrocatalysts. In general, a pyrolyzed electrocatalyst is subjected to a number of harsh treatments in order to remove different moieties. The chemical treatments selected may be, for example, those that are viewed as destructive to particular components of the overall electrocatalyst composition. Catalytic studies may then be performed with the materials after the treatments. Alternatively, or additionally, XPS characterization of the changes in electrocatalyst structure may be performed. The ORR catalytic activity and peroxide yields may be determined, for example, via rotating ring-disk electrode (RRDE). Characterization of the changes in surface chemistry that occur as a function of electrocatalyst production, modification and aging requires identification of subtle changes in complex systems. Scanning electron microscopy (SEM) and X-ray photoelectron spectroscopy (XPS) can be used to elucidate the structure of the electrocatalysts. Analysis of chemical bonding information from XPS spectra frequently utilizes deconvolution of the spectra into multiple peaks, resulting in significant interpretational ambiguities. Multivariate analysis (MVA) techniques, in combination with conventional curve fitting, facilitate both interpretation of the data and the development of structure-property correlations. Principal component analysis (PCA) can be applied to the XPS curve fits from the electrocatalysts, enabling identification of chemical species as a function of electrocatalyst treatment and correlation with electrochemical performance.

FIG. 7 is a schematic flowchart of an exemplary study showing the different electrocatalyst modifications and the characterization techniques.

FIGS. 8a-8d show high-resolution Co2p (FIG. 8a), O1s (FIG. 8b), N1s (FIG. 8c) and C1s (FIG. 8d) XPS spectra acquired for CoTMPP and all the altered electrocatalysts. The CoTMPP was pyrolyzed at 700° C.

Figure 8A:
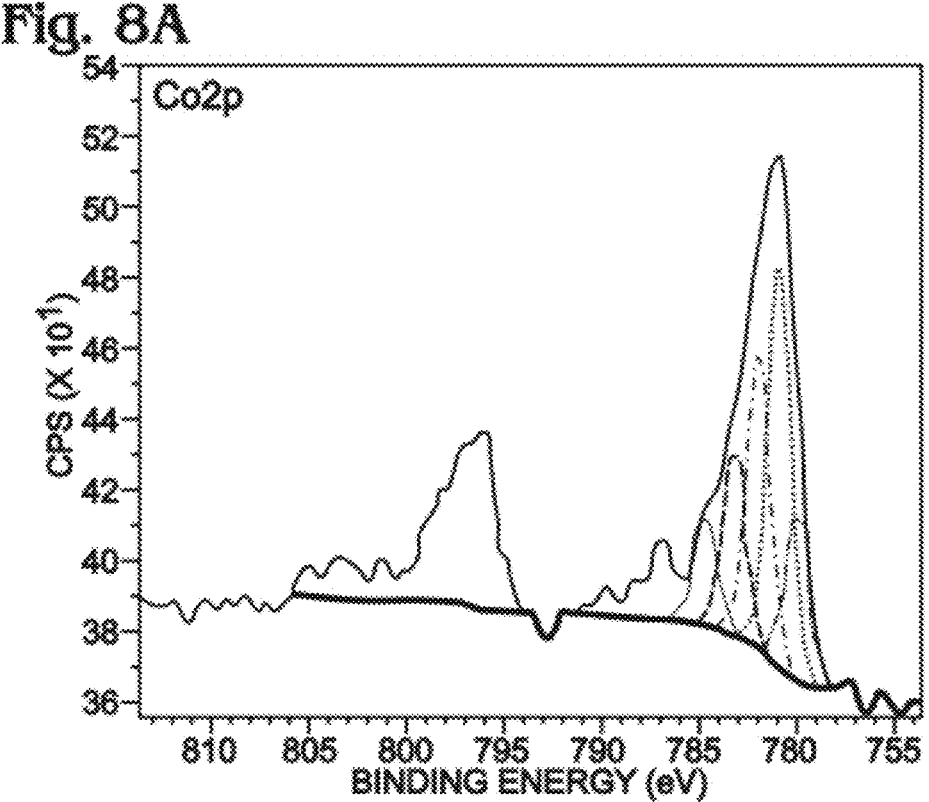
FIG. 8a is a high-resolution Co2p spectra of CoTMPP pyrolyzed at 700° C.

The five peaks that are required to fit Co 2p spectrum in FIG. 8a are located at 780, 780.9, 782, 783 and 785 eV. Cobalt oxides of different valencies ($Co_2O_3$, CoO and their mixture Co3O4) and metallic cobalt contribute to the XPS signal at 780 and 780.9 eV. The peak at 782 eV represents cobalt in Co—N4 centers. The assignment of the peaks at 783 and 785 eV are possibly some type of cobalt bound to oxygen in $Co(CO)_4$, but requires additional information from the other required spectra.

TABLE A

Specs for available silica templates

| product # | Supplier | product | BET specific surface area m2/g | pore size nm |
|---|---|---|---|---|
|  | UNM ChNE | mesoporous | 1500 | 4 or 2.6 |
| 420778 | Sigma-Aldrich | LUDOX TM-50 | 140 |  |
| 637246 | Sigma-Aldrich | nanopowder | 620 |  |
| 637328 | Sigma-Aldrich | nanopowder | 160 |  |
| 541036 | Sigma-Aldrich | mesoporous | n/a | 3.9 |
| 643637 | Sigma-Aldrich | mesoporous | 750 | 7.1 |
| 643645 | Sigma-Aldrich | mesoporous | 1000 | 2.7 |

Figure 8B:
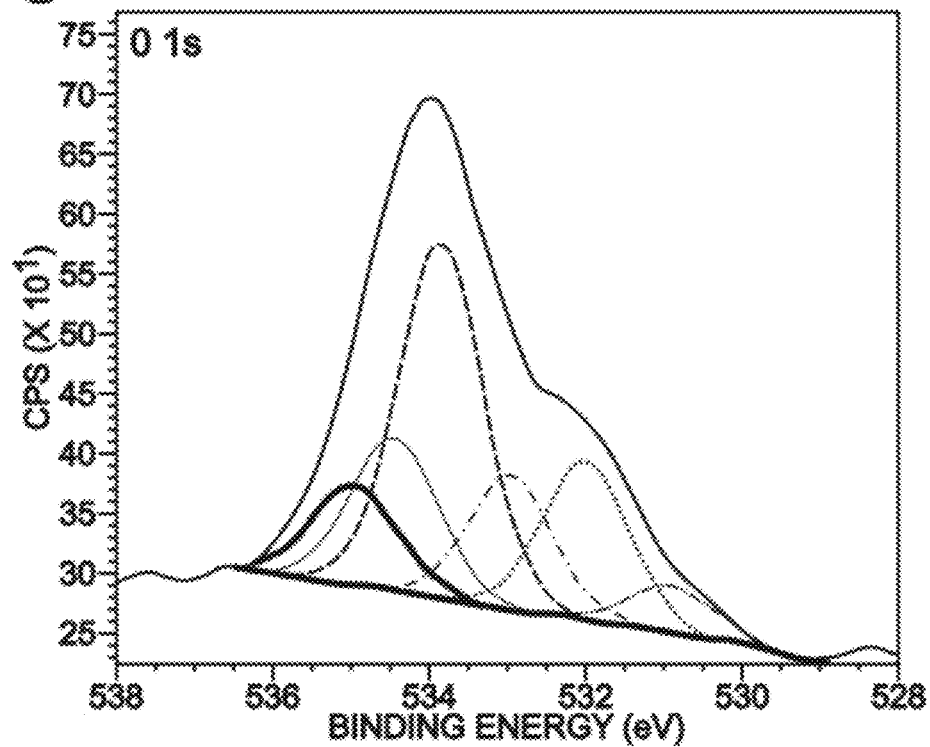
FIG. 8b is a high-resolution O1s spectra of CoTMPP pyrolyzed at 700° C.

The main peak in the O1s spectrum in FIG. 8*b* are located at 533.8 eV (32%) is due to CH3-O species, side chain of the CoTMPP. Peaks at 532 eV (17%) and 530.9 eV (8%) can be assigned to various cobalt oxides with contributions from O=C—N type of carbon. Multiple types of species containing oxygen, nitrogen and carbon (such as C=O, C—O, C—O—N types in moieties such as of bonding in CH4NO2 and Co(CO)4) are detected at binding energies of 533 and 535 eV.

Figure 8C:
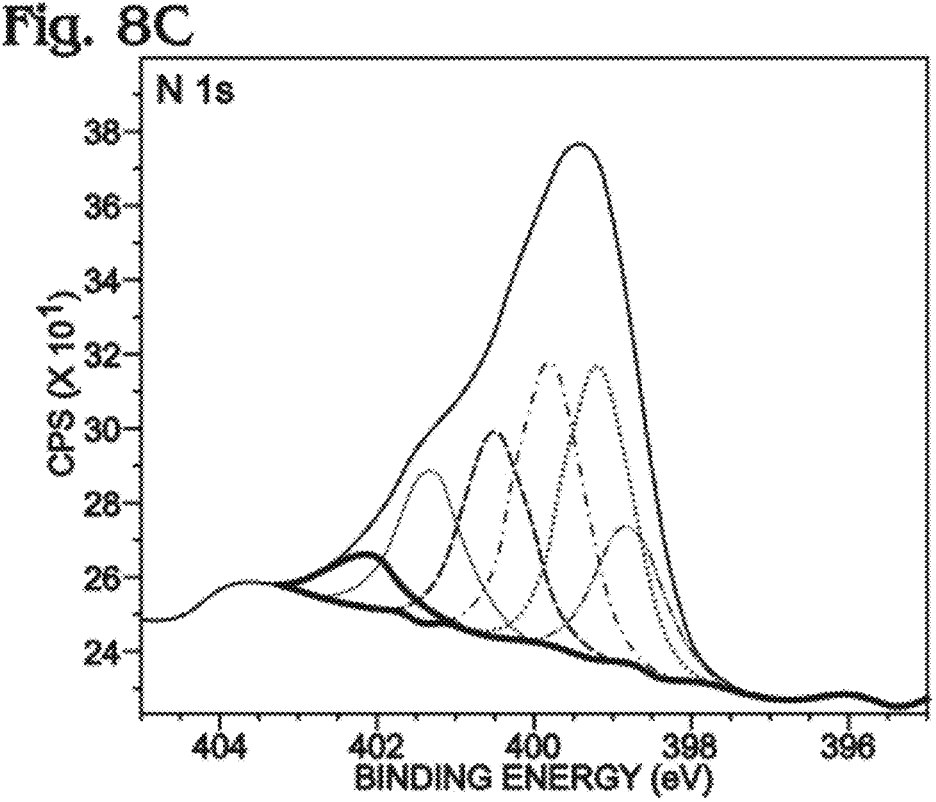
FIG. 8c is a high-resolution N1s spectra of CoTMPP pyrolyzed at 700° C.

The N1s spectrum in FIG. 8*c* was curve-fitted using 6 peaks. Two main components of the N1s spectrum, peaks at 399.2 and 399.8 eV, are due to Co—N centers and pyrollic nitrogen respectively. Pyridinic nitrogen is identified at 398.8 eV. Nitrogen peaks are also located at 400.5, 401.3 and 402.2 eV and can be assigned to C—N=O, "graphitic" nitrogen, and quaternary amine $(N(CH_3)_3)^+$, respectively.

Figure 8D:
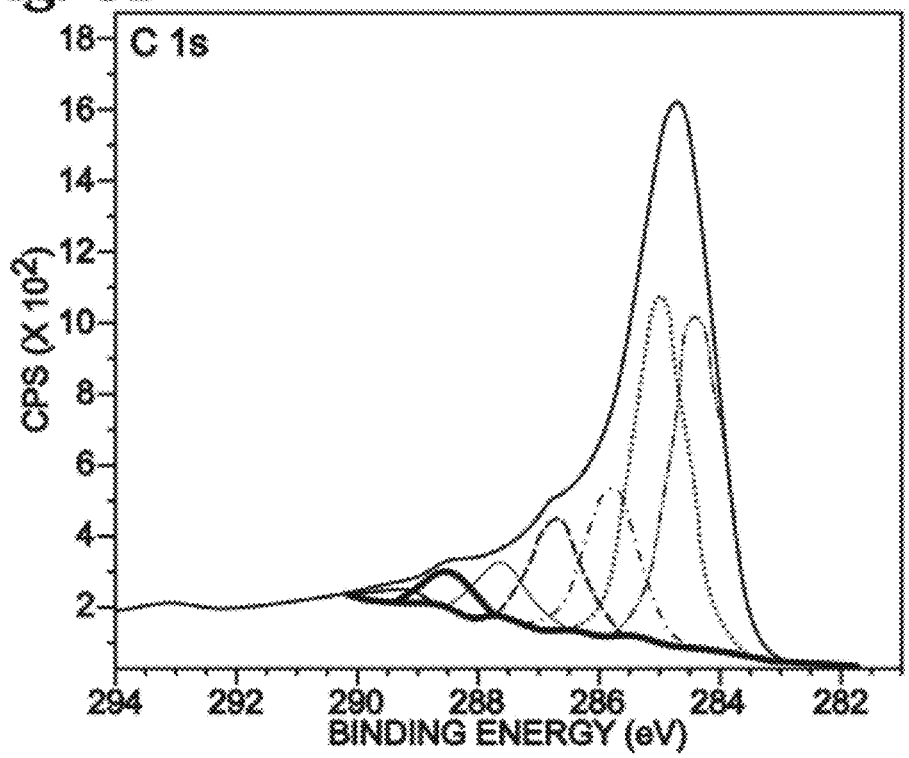
FIG. 8d is a high-resolution C1s spectra of CoTMPP pyrolyzed at 700° C.

There are 7 types of carbon species detected in the pyrolyzed CoTMPP. Turning to FIG. 8*d*, about 60% of the carbon is almost evenly divided between aromatic carbon, the main component of unpyrolyzed CoTMPP, and unsaturated carbon with graphite-like structure. Part of carbon is bound to nitrogen in C—N centers, including C—N centers present in the unpyrolyzed CoTMPP, pyrollic and pyridinic types of nitrogens. The peak at 286.7 eV is carbon bound to oxygen in O—CH3 side chain. Species that contribute to spectra at 287.6, 288.5 and 289.4 eV are oxygen and oxygen-nitrogen containing species such as C=O, C—N=O, which are also detected in the N1s and O1s curve-fits.

The various treatments that CoTMPP was subjected to removed select moieties as well as altered the overall surface area of the electrocatalysts. BET surface area measurements were made and used to normalize the electrochemical performance. FIGS. 9*a*-9*b* show the Koutecky-Levich plots for all tested electrocatalysts. FIG. 9*a* shows peroxide oxidation at the ring electrode. FIG. 9*b* shows oxygen reduction at the disk electrode as a function of the square root of rotation speed. It can be observed that the peroxide oxidation at the ring of the ring-disk electrode assemble reaches kinetic limiting current before the disk. This is most likely due to the peroxide being generated and then becoming trapped in the pores of the electrocatalyst. All RRDE measurements were preformed within the kinetic limiting region.

Figure 10A:
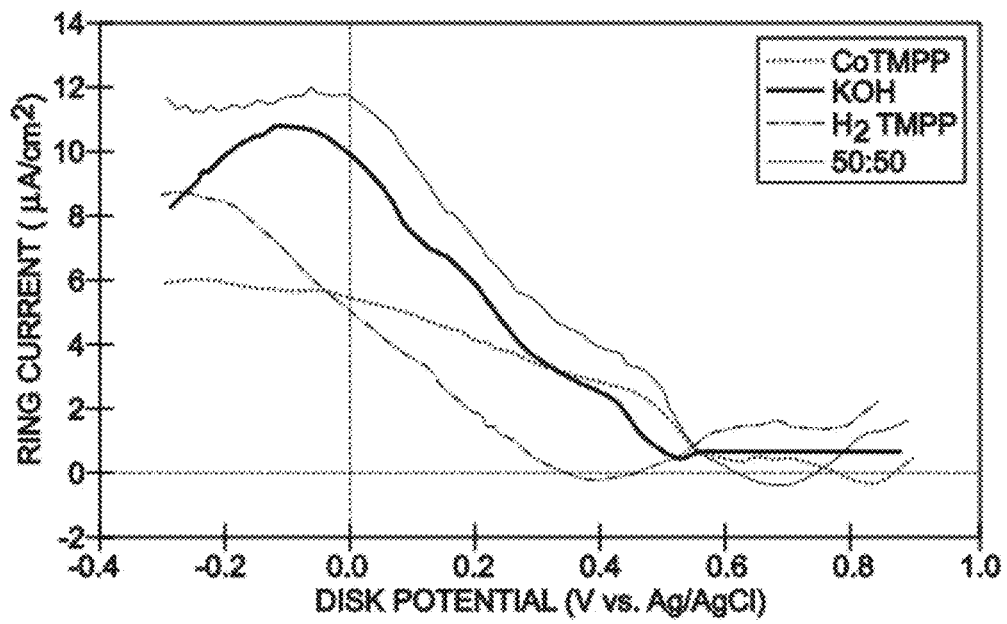
FIG. 10a shows RRDE data obtained in oxygen saturated 0.5 M $H_2SO_4$, electrocatalyst loading of 68 μg, normalized to BET surface area, room temperature, 6000 RPM, ring held at 1.1V vs. Ag/AgCl.
Figure 10B:
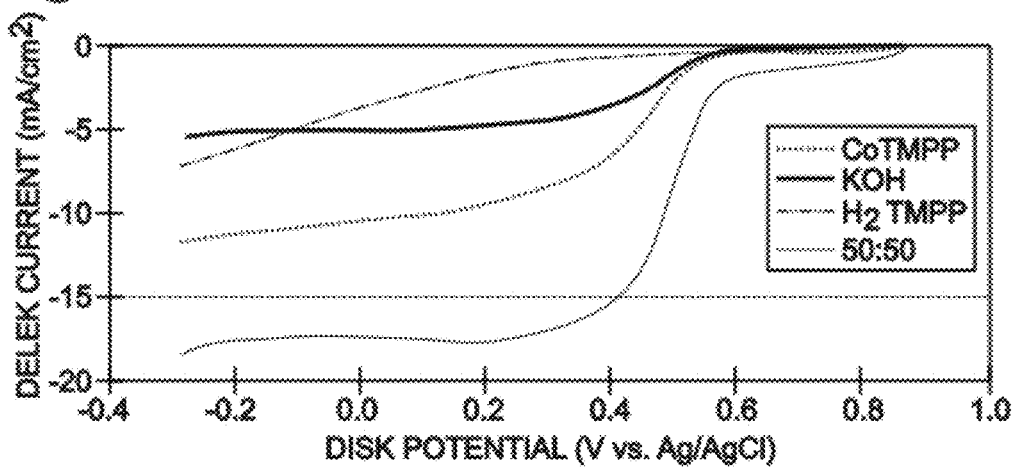
FIG. 10b shows RRDE data obtained in oxygen saturated 0.5 M $H_2SO_4$, electrocatalyst loading of 68 μg, normalized to BET surface area, room temperature, 6000 RPM, disk scanned at 10 mV/s.

FIGS. 10*a*-10*b* show RRDE data for pyrolyzed CoTMPP, KOH treated CoTMPP, H2TMPP, and the 50:50 wt % CoTMPP:H2TMPP. The individual ORR activity as well as the peroxide generation for each electrocatalyst can be directly compared to the CoTMPP electrocatalyst. The $H_2$TMPP electrocatalyst shows lower ORR limiting current as well as a more negative "kick-off" potential and more peroxide generation. These results indicate that cobalt moieties are responsible for the catalyzed ORR and shifting the mechanism towards 4 e– reduction. Comparison of the KOH treated electrocatalyst with the CoTMPP electrocatalyst shows the KOH treatment results in lower ORR and higher peroxide production. From XPS analysis it is known that the KOH treatment material is deficient in cobalt oxide species. Based on structural analysis and RRDE performance it is concluded that the KOH treated material shifts the ORR mechanism towards the peroxide pathway. Finally, the 50:50 wt % CoTMPP:H2TMPP shows increased ORR limiting current and peroxide generation. This is a very interesting result knowing that there is only half (by weight) of the total amount of cobalt present in the electrocatalyst compared to CoTMPP.

FIGS. 11*a* and *b* show SEM images of CoTMPP (FIG. 11*a*) and the 50:50 wt % CoTMPP:$H_2$TMPP (FIG. 11*b*). The micrograph of CoTMPP shows that the cobalt particles cover a majority of the surface while the cobalt particles decorating the 50:50 wt % CoTMPP:$H_2$TMPP electrocatalyst are much smaller and more dispersed.

Figure 12:
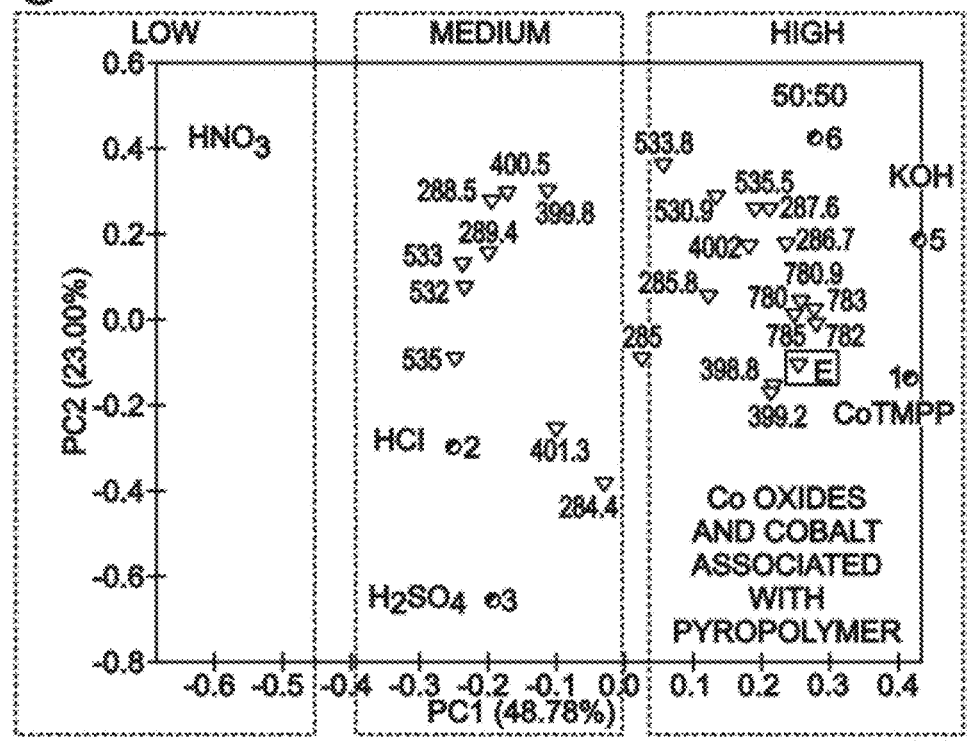
FIG. 12 shows a biplot that has been divided into three groups of high, medium, and low ORR activity.

FIG. 12 shows a biplot that has been divided into three groups of high, medium, and low ORR activity. The first group combines samples with relatively high oxygen reduction activity (CoTMPP, 50:50, KOH). HCl and $H_2SO_4$ treated samples form the group with medium oxygen reduction activity. And finally, the last group, $HNO_3$ treated sample, shows the lowest oxygen reduction activity. The established correlations suggest that for high oxygen reduction activity, materials must have cobalt in oxide form and cobalt associated with pyropolymer. Removal of one and/or both of types of cobalt lowers oxygen reduction activity.

Based on these structure-to-performance correlations and the experimental RRDE data the ORR mechanism that occurs on pyrolyzed CoTMPP can be proposed. FIG. 13 illustrates the proposed ORR mechanism where oxygen is first reduced to peroxide at an active site on the pyropolymer (cobalt associated with nitrogen) and then further reduced to water on a decorating cobalt particle. To shift the overall ORR mechanism toward the 4 e– pathway it is essential to engineer a dispersed cobalt particle phase.

The turn over frequency (TOF) can now be estimated based on the mechanistic information gained from this study. In order to estimate the TOF a number of assumptions need to be made.

a. Half of the cobalt remains associated with nitrogen in the pyropolymer.
b. Half of the cobalt is found in the cobalt particle phase.
c. All cobalt-nitrogen species ($CoN_4$, $CoN_3$, $CoN_2$, CoN) in the pyropolymer have the same ORR TOF.
d. Pyropolymer active site density can be estimated with precursor molecular size (approximately 1 $nm^2$).
e. Diffusion resistance through Nafion film is negligible.
f. All possible active sites are accessible in RRDE experiments.

The calculation for the TOF at 0.2 V vs. Ag/AgCl for the KOH treated CoTMPP electrocatalyst is shown.

$$\frac{\text{Current density}\left(\frac{A}{m^2}\right)}{1.6 \times 10^{-19}\left(\frac{C}{e^-}\right)} = \frac{e^-}{\text{site } s}$$

Assuming that the active sites are cobalt moieties that are associated with nitrogen and half of the precursor cobalt centers remain the site density is calculated to be $2.5 \times 10^{17}$ sites/$m^2$.

$$\frac{\frac{5 \times 10^{-7}\left(\frac{A}{m^2}\right)}{1.6 \times 10^{-19}\left(\frac{C}{e^-}\right)}}{2.5 \times 10^{17}\left(\frac{\text{sites}}{m^2}\right)} = 1.3 \times 10^{-5}\left(\frac{e^-}{\text{site } s}\right)$$

Therefore, the TOF for the electrochemical conversion of oxygen to peroxide on cobalt associated with nitrogen sites is shown to be $1.3 \times 10^{-5}$. Similar analysis was preformed for the $H_2$TMPP electrocatalyst and a TOF of $1.25 \times 10^{-6}$ TOF was calculated. It is more difficult to calculate TOF when a duel site mechanism is present. Although, it can be observed that the current was almost 2 and 3.5 times greater for CoTMPP and 50:50 wt % CoTMPP:H$_2$TMPP, respectively. The increase in current is contributed to the reduction of peroxide to water on the cobalt particle species. TOF values can be converted to exchange current density by dividing by the Faraday constant.

Evaluating and optimizing the performance of an ORR electrocatalysts under realistic working fuel cell conditions is essential in electrocatalyst selection and development. The catalytic layer in a MEA consists of electrocatalyst, carbon black, and Nafion. For optimal performance the three phase interface (electrocatalyst, electrolyte, and reactant) must be well dispersed thought out the active layer.

According to another embodiment, the present disclosure provides a semi-factorial approach to optimize the composition of the catalytic layer. This approach can greatly reduce the number of combinations of the component loadings. For example, a full factorial design of experiments consisting of 3 components at 3 different loadings each results in 27 possible combinations. The technique used here can reduce the number of combinations to as few as 9 for the same 3 by 3 matrix. This is done by optimizing one parameter loading at a time using an iterative method if needed. For example, first select the 3 parameter loadings which are believed to be optimal or close to optimal. Then each parameter is individually optimized by testing the performance at loading values above and below the optimal value. This process is continued for the other two parameters. Iteration is needed if a parameter loading value is found not to optimal. This methodology is used to determine the optimal electrocatalyst loading for the batch pyrolyzed CoTMPP, Teflon treated Vulcan XC-72 carbon black, containing 35 wt. % Teflon (XC-35), and Nafion content in the active layer.

Figure 14:
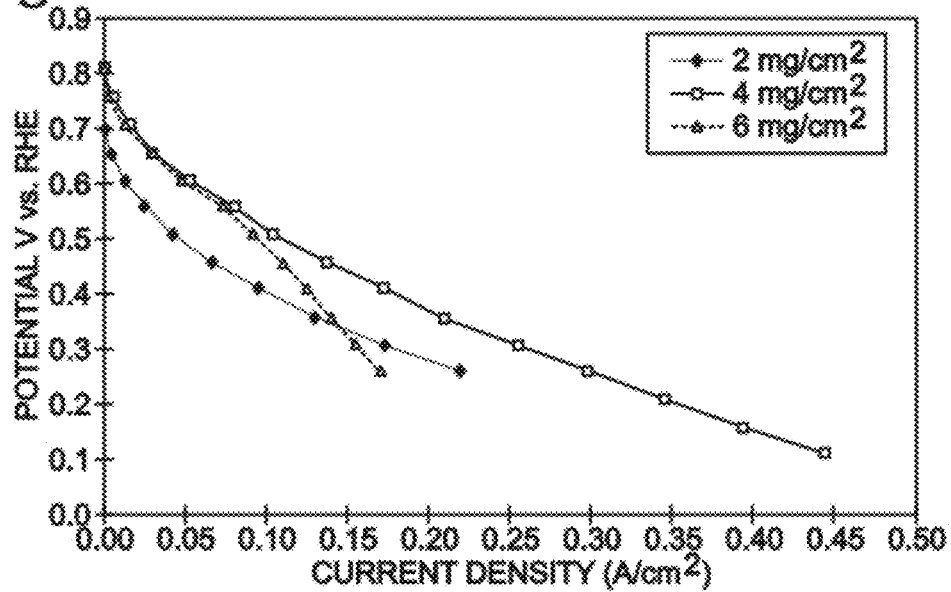
FIG. 14 displays the optimization of CoTMPP electrocatalyst loading.
Figure 15:
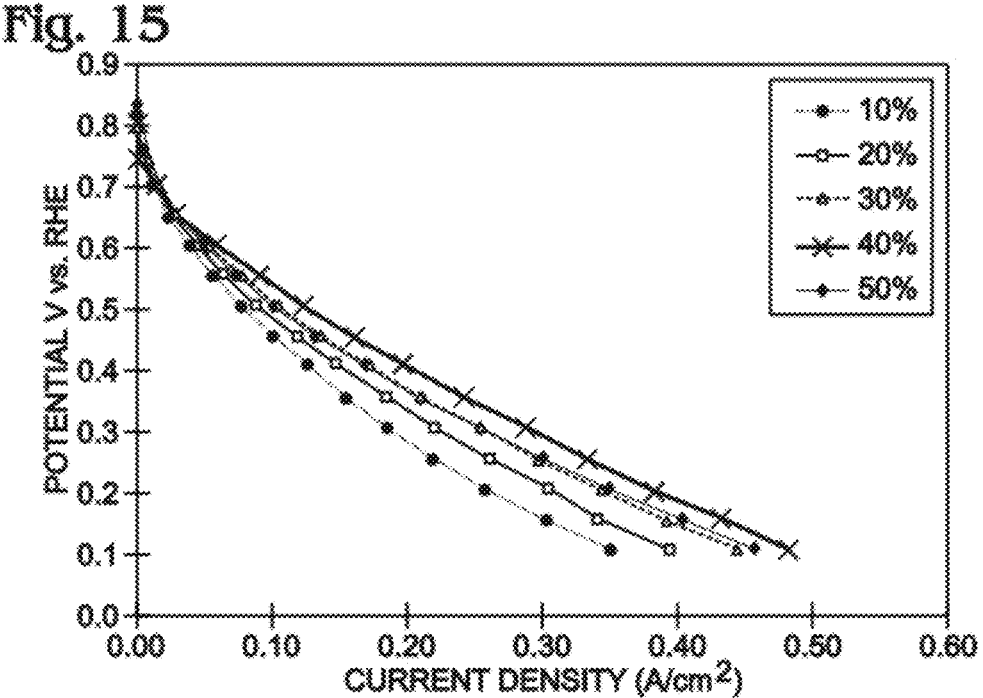
FIG. 15 displays the optimization of CoTMPP Teflon-treated carbon blacks (XC-35) loading.
Figure 16:
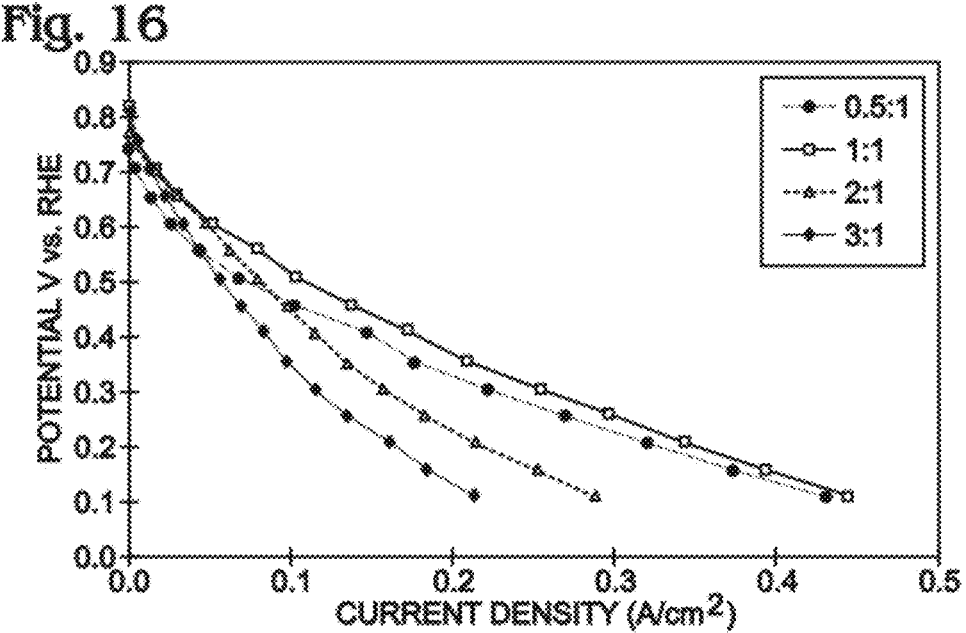
FIG. 16 displays the optimization of CoTMPP Nafion to electrocatalyst ratio.

FIG. 14 displays the optimization of CoTMPP electrocatalyst loading. Peak performance is obtained at 4 mg/cm$^2$ electrocatalyst loading, 40% Teflon-treated carbon blacks (XC-35) loading, and electrocatalyst and 1:1 Nafion to electrocatalysts ratio. Operating conditions are H2/air, 80° C., and 0 back pressure. First the electrocatalyst loading was optimized by beginning with what is believed to be the optimal electrocatalyst layer composition of 4 mg/cm$^2$ CoTMPP electrocatalyst, Teflon-treated carbon blacks, XC-35 loading of 40 wt % to electrocatalysts loading (1.6 mg/cm$^2$), and a 1:1 Nafion to electrocatalyst weight ratio. The electrocatalyst loading was varied at 2, 4, and 6 mg/cm$^2$ while the Teflon-treated carbon blacks, XC-35 and Nafion content was held constant. FIG. 15 displays the optimization of CoTMPP and Teflon-treated carbon blacks XC-35 loading. Peak performance is obtained at 40% of Teflon-treated carbon black XC-35 loading, 4 mg/cm2 electrocatalyst and 1:1 Nafion to electrocatalysts ratio. Operating conditions were H2/air, 80° C., and 0 back pressure. FIG. 15 shows that peak performance is obtained with 4 mg/cm2 CoTMPP electrocatalyst loading. The Teflon-treated carbon blacks, XC-35 loading was then optimized while holding the electrocatalyst loading and Nafion content constant at 4 mg/cm2 and 1:1 weight ratio, respectively. FIG. 15 further indicates that 40% of the electrocatalyst loading is most favorable. Finally, the Nafion to electrocatalyst weight ratio was optimized. FIG. 16 displays the optimization of CoTMPP Nafion to electrocatalyst ratio. Peak performance is obtained at 1:1 Nafion to electrocatalysts ratio, 40% Teflon-treated carbon blacks XC-35 loading, and 4 mg/cm$^2$ electrocatalyst. Operating conditions were H2/air, 80° C., and 0 back pressure. FIG. 16 shows that the 1:1 weight ratio has the best performance.

Figure 17:
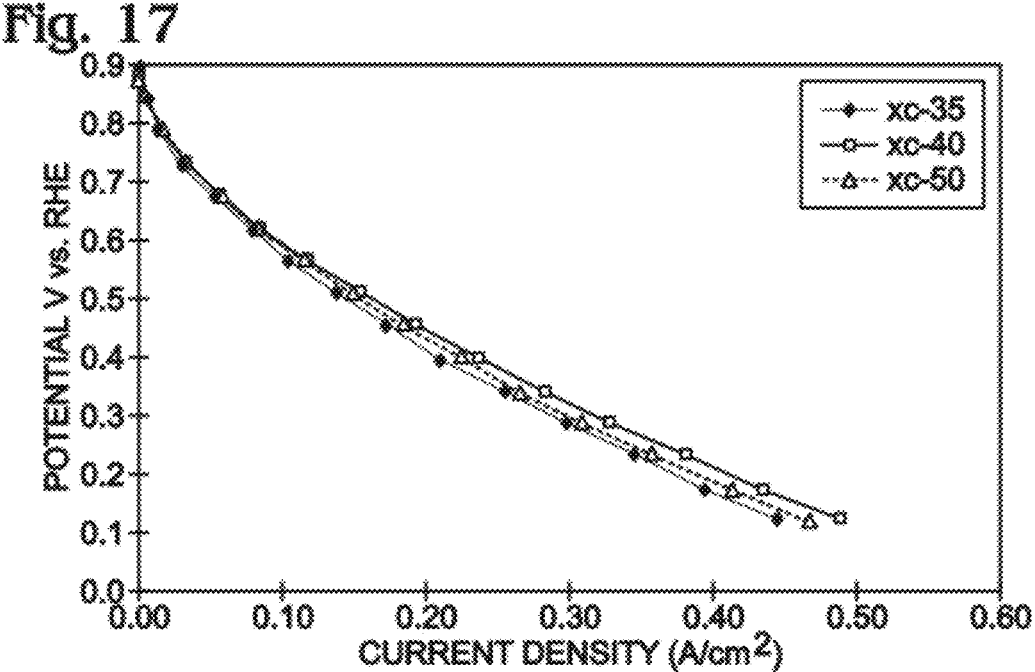
FIG. 17 shows the performance with Vulcan XC-72 carbon black with different Teflon contents.

Alternative materials were tested in the MEA configuration using the optimized loading values. Carbon blacks (XC-75) with higher Teflon weight percents of 40% (XC-40) and 50% (XC-50) were tested. The Teflon coated carbon blacks not only provide added conductivity to the layer, but also supply hydrophobic pathways for oxygen transport through the layer and felicitate product water removal from active sites. FIG. 17 shows the performance with Vulcan XC-72 carbon black with different Teflon contents. The operating conditions were H2/air, 80° C., and 0 back pressure. Peak ORR performance is seen with the XC-40 material.

Further information on the processes that occur in the electrocatalyst layer during fuel cell operation can be exemplified with $\Delta E$ vs i analysis. $\Delta E$ vs i analysis is used to elucidate the transport hindrances that occur in the active layer that strongly influence the overall performance of the electrode. The analysis is done by first obtaining polarization curves in oxygen and air. Next, the difference of the potentials of the electrode while operating in oxygen and air at the same current density is taken. This difference in potentials is theoretically described by Equation 3.

$$\Delta E = E_{O_2}(i) - E_{air}(i) = \frac{RT}{\alpha nF}\ln\left(\frac{P_{O_2}}{P_{air}}\right) + \frac{RT}{\alpha nF}\ln\left(\frac{f_{O_2}(i)}{f_{air}(i)}\right) \quad \text{[Equation 3]}$$

Figure 18:
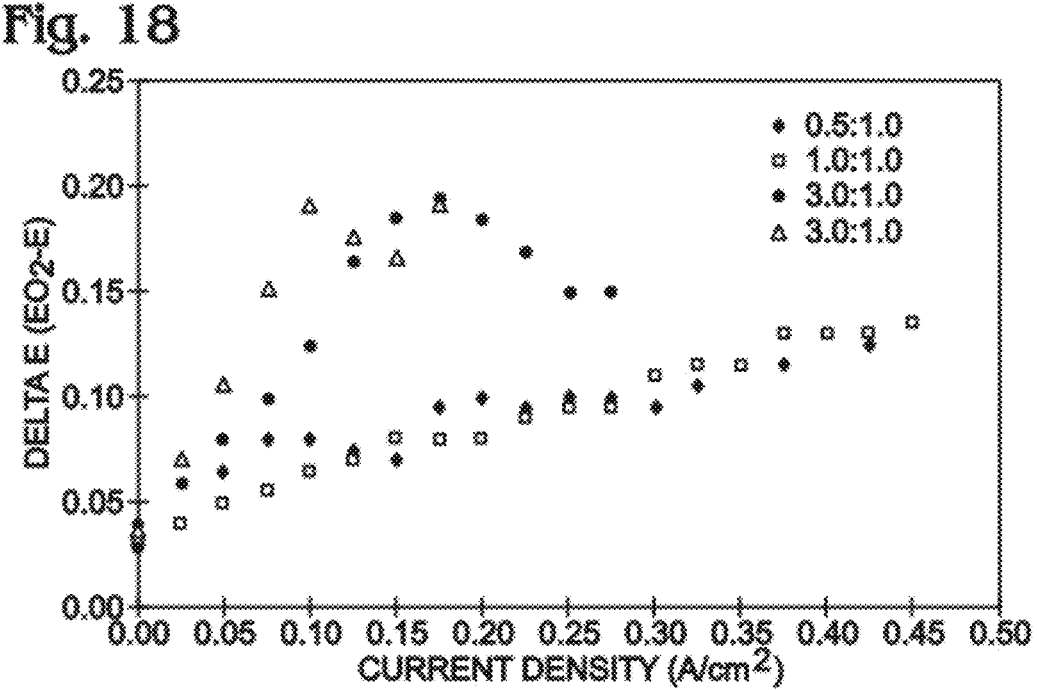
FIG. 18 shows ΔE vs i analysis for electrodes prepared with different Nafion to electrocatalysts ratios.

The first term is independent to current and shows the oxygen partial pressure dependence. The second term incorporates the dependence on current density with the efficiency factors for oxygen $f_{O_2}$ and air $f_{air}$. The efficiency factors are similar to effectiveness factor in that it is defined as the ratio of currents at a given potential for the real electrode and a hypothetical electrode with the same surface area and no transport losses. At high current densities the second term begins to increase because the efficiency of the electrode operated under air will decrease more rapidly than when under oxygen operation. FIG. 18 shows $\Delta E$ vs i analysis for electrodes prepared with different Nafion to electrocatalysts ratios. It can be observed that increased Nafion content produces significant transport hindrances at lower current densities.

Figure 19:
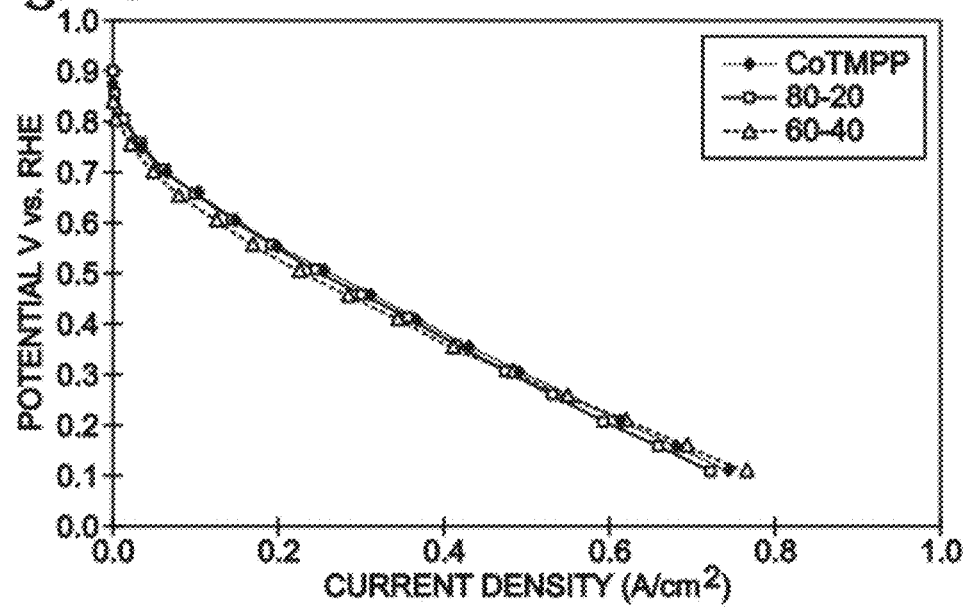
FIG. 19 shows H2/oxygen polarization for CoTMPP and 80:20 and 60:40 CoTMPP:$H_2$TMPP wt
Figure 20:
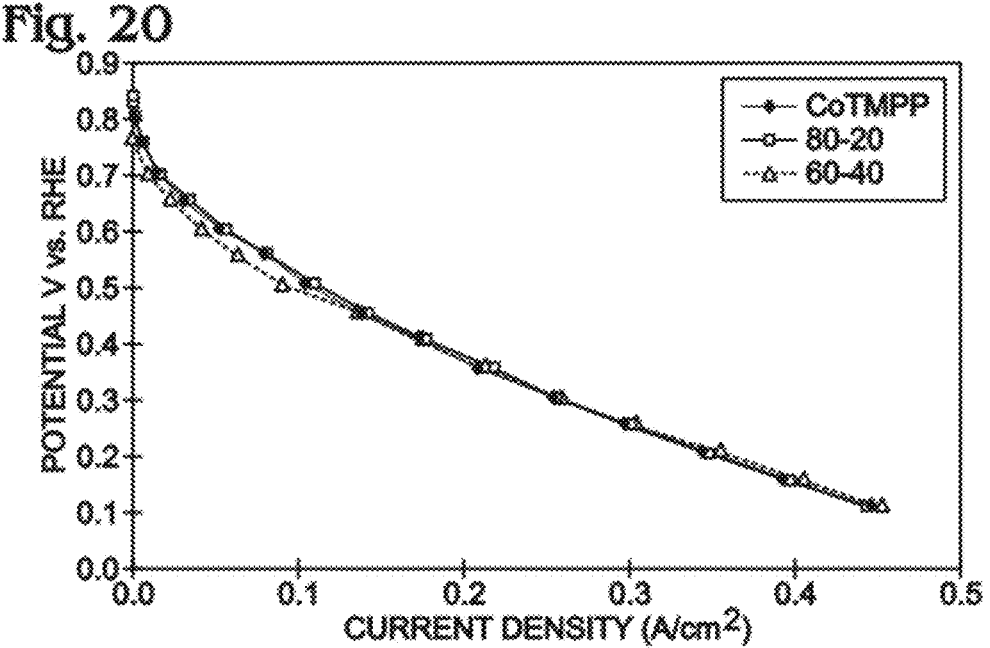
FIG. 20 shows H2/air polarization for CoTMPP and 80:20 and 60:40 CoTMPP:$H_2$TMPP wt %.

$\Delta E$ vs i analysis can also be used to support mechanistic hypotheses. Different electrocatalysts formulations were synthesized and tested in a MEA environment by pyrolyzing various mixtures of CoTMPP and H$_2$TMPP (80:20 and 60:40 weight ratios). FIGS. 19 and 20 show polarization curves for CoTMPP, 80:20 CoTMPP:H$_2$TMPP, and 60:40 CoTMPP:H$_2$TMPP electrocatalyst formulations obtained in oxygen and air, respectively. The Operating conditions for both FIGS. 19 and 20 were H2/oxygen, 80° C., and 0 back pressure. Under both conditions (oxygen and air) the electrocatalysts show almost identical performance and therefore the $\Delta E$ vs i curves would also be similar. Analysis of this result leads to a number of conclusions. First, that the electrocatalyst formulations have similar active site accessibility. Second, the 80:20 and 60:40 formulations result in a more dispersed cobalt particle phase but at the same time would contain less cobalt associated with nitrogen in the pyropolymer backbone. Therefore it is possible that one active site is being substituted for a more dispersed second active site.

The present disclosure has been provided with a plurality of different examples providing various conditions and experimental parameters. It will be understood that such examples are provided for the purposes of providing a better of understanding of various experimental conditions that could be used and that the present disclosure is not intended to be limited by these examples.

What is claimed is:

1. A method for producing a non-platinum electrocatalyst suitable for use in a fuel cell comprising:
    providing a plurality of removable template particles;
    precipitating a transition metal $N_4$-chelate precursor made of $H_2$ tetraphenyl porphyrin and cobalt tetraphenyl porphyrin onto the plurality of removable template particles to produce a dispersed precursor;
    pyrolyzing the dispersed precursor to produce a pyropolymer; and
    removing the template particles to produce a highly dispersed, self supported, high surface area electrocatalytic material.

2. The method of claim 1 wherein the plurality of removable template particles are silica-based.

3. The method of claim 2 wherein the silica-based template particles are amorphous silica.

4. The method of claim 2 wherein the silica-based particles are mesoporous.

5. The method of claim 2 wherein the silica-based template particles are removed by chemical etching.

6. The method of claim 1 wherein the removable template particles and $N_4$-chelate precursors are selected for use so as to shift the reaction mechanism of the electrocatalytic material towards the 4 e– pathway.

7. The method of claim 1 further comprising selecting removable template particles to use so as to produce electrocatalytic material with a desired pore size.

8. A highly dispersed, unsupported catalytic material substantially consisting of pyrolyzed porphyries manufactured using the method of claim 1.

9. A highly dispersed, unsupported catalytic material substantially consisting of pyrolyzed porphyries formed from a precursor made of $H_2$ tetraphenyl porphyrin and cobalt tetraphenyl porphyrin.

10. The material of claim 9 comprising pores between 3 nm and 10 nm in diameter.

11. The material of claim 9 comprising pores between 30 nm and 70 nm in diameter.

12. The material of claim 9 comprising cobalt atom centers bonded to one, two, three, or four nitrogen atoms in the $2^+$ form and cobalt particles coated in a thin oxide film deposited on the pyropolymer backbone.

* * * * *

Disclaimer

8,252,711 B1 — Tim Olson, Albuquerque, NM (US); Plamen Atanassov, Albuquerque, NM (US). SELF SUPPORTING STRUCTURALLY ENGINEERED NON-PLATINUM ELECTROCATALYST FOR OXYGEN REDUCTION IN FUEL CELLS. Patent dated August 28, 2012. Disclaimer filed July 25, 2014, by the inventors.

Hereby disclaims term of this patent which shall not extend beyond the expiration date of Patent No. 7,678,728.

*(Official Gazette, October 21, 2014)*